(12) United States Patent
Eagleman et al.

(10) Patent No.: US 9,626,845 B2
(45) Date of Patent: Apr. 18, 2017

(54) PROVIDING INFORMATION TO A USER THROUGH SOMATOSENSORY FEEDBACK

(71) Applicants: Baylor College of Medicine, Houston, TX (US); William Marsh Rice University, Houston, TX (US)

(72) Inventors: David M. Eagleman, Houston, TX (US); Scott Novich, Dallas, TX (US)

(73) Assignee: Baylor College of Medicine William Marsh Rice University, Houston, TX (US)

(*) Notice: Subject to any disclaimer, the term of this patent is extended or adjusted under 35 U.S.C. 154(b) by 0 days.

(21) Appl. No.: 14/750,626

(22) Filed: Jun. 25, 2015

(65) Prior Publication Data

US 2016/0012688 A1    Jan. 14, 2016

Related U.S. Application Data (60) Provisional application No. 62/022,478, filed on Jul. 9, 2014.

(51) Int. Cl.
*H04B 3/36* (2006.01)
*G08B 6/00* (2006.01)
(Continued)

(52) U.S. Cl.
CPC ............... *G08B 6/00* (2013.01); *A61F 11/04* (2013.01); *G06F 3/016* (2013.01); *G09B 21/003* (2013.01)

(58) Field of Classification Search
CPC ......... G08B 6/00; G06F 3/016; G09B 21/003; A61F 11/04
(Continued)

(56) References Cited

U.S. PATENT DOCUMENTS

| 4,926,879 A | * | 5/1990 | Sevrain | G08B 6/00 340/407.1 |
| 7,979,146 B2 | * | 7/2011 | Ullrich | G06F 3/016 340/407.1 |

(Continued)

FOREIGN PATENT DOCUMENTS

| WO | 2008106698 A1 | 9/2008 |
| WO | 2012069429 A1 | 5/2012 |

OTHER PUBLICATIONS

Plant, Geoff, "Training in the use of the Tactaid VII: A case study", KTH Computer Science and Communication (STL-QPSR), 1994, vol. 35, No. 1, pp. 091-102.

*Primary Examiner* — John A Tweel, Jr.
(74) *Attorney, Agent, or Firm* — Jeffrey Schox; Ivan Wong (57) ABSTRACT

A hearing device may provide hearing-to-touch sensory substitution as a therapeutic approach to deafness. Through use of signal processing on received signals, the hearing device may provide better accuracy with the hearing-to-touch sensory substitution by extending beyond the simple filtering of an incoming audio stream as found in previous tactile hearing aids. The signal processing may include low bitrate audio compression algorithms, such as linear predictive coding, mathematical transforms, such as Fourier transforms, and/or wavelet algorithms. The processed signals may activate tactile interface devices that provide touch sensation to a user. For example, the tactile interface devices may be vibrating devices attached to a vest, which is worn by the user. The vest may also provide other types of information to the user.

28 Claims, 8 Drawing Sheets

(51) Int. Cl.
*G06F 3/01* (2006.01)
*G09B 21/00* (2006.01)
*A61F 11/04* (2006.01)

(58) Field of Classification Search
USPC .......................................... 340/407.1, 691.1
See application file for complete search history.

(56) References Cited

U.S. PATENT DOCUMENTS

| | | | | |
|---|---|---|---|---|
| 8,068,025 | B2* | 11/2011 | Devenyi | H04R 1/1041 340/407.1 |
| 8,754,757 | B1* | 6/2014 | Ullrich | G06F 3/016 340/407.1 |
| 9,019,087 | B2* | 4/2015 | Bakircioglu | G06F 3/016 340/407.1 |
| 9,298,260 | B2* | 3/2016 | Karaoguz | G06F 3/016 |
| 2007/0041600 | A1 | 2/2007 | Zachman | |
| 2011/0063208 | A1* | 3/2011 | Van Den Eerenbeemd | G06F 3/016 340/407.1 |
| 2013/0218456 | A1* | 8/2013 | Zelek | G01C 21/00 701/411 |

* cited by examiner

PROVIDING INFORMATION TO A USER THROUGH SOMATOSENSORY FEEDBACK

CROSS-REFERENCE TO OTHER PATENT APPLICATIONS

This application claims the benefit of priority to U.S. Provisional Patent Application No. 62/022,478 to Eagleman et al. filed on Jul. 9, 2014 and entitled "PROVIDING INFORMATION TO A USER THROUGH SOMATOSENSORY FEEDBACK," which is incorporated by reference herein.

GOVERNMENT LICENSE RIGHTS

This invention was made with government support under Grant #5T32EB006350-05 awarded by National Institutes of Health (NIH). The government has certain rights in the invention.

FIELD OF THE DISCLOSURE

The instant disclosure relates to providing information through touch sensation. More specifically, this disclosure relates to high-information rate substitution devices (such as, for hearing).

BACKGROUND

There are at least 2 million functionally deaf individuals in the United States, and an estimated 53 million worldwide. Auditory perception is an important part of an individual's integration into society because much of a person's interactions with other people and electronic and mechanical devices is through audible information. For deaf individuals, conversing with friends and family, interacting with mobile devices, watching television, and hearing cars and other nearby machinery can be difficult or impossible. Without auditory perception, deaf individuals face operational difficulties, entertainment difficulties, and safety difficulties.

One conventional tool available for deaf individuals is the cochlear implant. However, cochlear implants (CI) are not a viable hearing solution for a large fraction of the deaf individuals. One reason is cost: as a lower bound, the overall cost of a CI implantation procedure and subsequent follow-ups is $40,000. This places CIs out of economic reach for many. Additionally, CIs require an invasive surgery. Furthermore, CIs have limited benefits in early-onset deaf adults who are receiving the CI after the age of 12. Thus, not only is the CI expensive and the implantation a dangerous surgical process, but the CI must be implanted while the individual is young. This limits options for deaf individuals who seek auditory perception later in life.

The problems described above underscore the need for a low-cost, non-invasive hearing solution, and one that can work for adults who have been deaf since birth. One conventional solution is to use sound-to-touch sensory substitution devices. However, a successful sound-to-touch sensory substitution device has yet to be developed. Sound-to-touch devices as an aid for hearing have been researched in the past. However, such devices have been unable to achieve a sufficient efficacy to act as a full substitution for hearing and instead only act as a hearing "aid," rather than as a substitution device. These devices generally rely on band-pass filtering an audio signal and playing this filtered output to the skin over vibrating solenoids. These solenoids operate at a fixed frequency of less than half the bandwidth of some of these band-passed channels, leading to aliasing noise. Thus, the touch representation of received audio sounds is inaccurate and also insufficiently accurate enough to provide a substitute for hearing the audio sounds. Furthermore, the limited bandwidth available for conveying information restricts the application of these prior sound-to-touch substitution devices to only low-bandwidth audio applications, without the ability to convey high-throughput data.

SUMMARY

A somatosensation feedback device may provide information to a user by transforming and/or compressing the information and mapping the information to an array of devices in the somatosensation feedback device. In one embodiment, the somatosensation feedback device may be a wearable item or embedded in wearable clothing, such as a vest. The vest may include an array of feedback devices that provide somatosensation feedback, such as vibration or motion. The vibration or motion may convey the transformed and/or compressed information to the user.

In one embodiment, the vest may be used as a hearing device to provide audio-to-touch transformation of data. The hearing device may provide hearing-to-touch sensory substitution as a therapeutic approach to deafness. Through use of signal processing on received signals, the hearing device may provide better accuracy with the hearing-to-touch sensory substitution by extending beyond the simple filtering of an incoming audio stream as found in previous tactile hearing aids. The signal processing may include low bitrate audio compression algorithms, such as linear predictive coding, mathematical transforms, such as Fourier transforms, and/or wavelet algorithms. The processed signals may activate tactile interface devices that provide touch sensation to a user. For example, the tactile interface devices may be vibrating devices attached to a vest, which is worn by the user. Through use of the signal processing and mapping of processed signals to tactile interface devices, a deaf individual may learn to interpret skin sensations as audible speech and sounds.

The signal processing for activating tactile interface devices may be performed in real-time through a controller integrated with tactile interface devices or from a separate computing device, such as a smart phone, tablet computer, laptop computer, MP3 player, and/or voice recorder. Users often have one of these computing devices with them, and such a computing device may be used to provide signal processing for the tactile interface devices. In addition to vibrotactile stimulation, electrotactile stimulation, such as against bare skin, may be used provide information transfer through somatosensation. Whether the vest incorporates electrotactile, vibrotactile, or other stimulation, the vest may provide a wearable sound-to-touch sensory substitution system designed for perceiving auditory information, possibly without adjunct information, such as lip reading.

A wearable hearing-to-touch sensory substitution, such as in the embodiments described in further detail below, may cost less than one thousand dollars and provide hearing substitution without the invasive and dangerous surgery required by cochlear implants (CIs). Further, such a device may benefit deaf adults who were born deaf, a group of individuals for who CIs do not work well. Further, the signal processing, described in further detail below, may overcome temporal limitations of skin-based sensory perception through the use of mathematical transforms and/or parametric modeling. The system for providing hearing-to-touch sensory substitution may also be configured to provide other data, including news, financial information, caller identification, message notification, or the like, to the user through somatosensation.

According to one embodiment, an apparatus may include one or more microphones, an array of tactile interface devices, and a processing module coupled to the array of tactile interface devices and coupled to the microphone. The processing module may be configured to perform the steps of receiving audio samples of an audio signal from the microphone; transforming, such as by decomposing, the audio samples from a time domain to a space domain; compressing the transformed audio samples; and/or generating control signals for operating the array of tactile interface devices by mapping the compressed audio samples to individual devices of the array of tactile interface devices.

According to another embodiment, a method may include receiving samples of a data signal; transforming the samples from a time domain to a space domain; compressing the transformed samples; and/or generating control signals for operating an array of tactile interface devices by mapping the compressed samples to individual devices of the array of tactile interface devices.

Although many examples may be provided regarding processing audio for feedback through the tactile interface devices, the disclosed methods are agnostic of the type of data being provided to a user through the tactile interface devices. For example, stock, weather, or other data available through the Internet may be conveyed to a user through the tactile interface devices. Processing of non-audio data may be performed very similarly to processing of audio data. The process may include first obtaining data over a desired duration, such as a window of a particular size or length of data such as 5 milliseconds or 5 kilobytes or 128 samples, and then perform either a signal decomposition or a feature extraction. Signal decomposition allows for the reconstruction of the original signal (if enough information is captured), such as with a discrete cosine transform (DCT), auto-encoding neural network, Fast Fourier Transform (FFT), and/or wavelets. Feature extraction may include finding desired information within the signal, although the extracted features may not be enough to reproduce or recreate the originally-obtained data in full, such as linear predictive filtering or coding or Mel Frequency Cepstral Coefficients. Then, for each frame of data, the decomposition or feature extraction algorithm may produce a set of numbers that represent the obtained data in either a lossless or lossy manner. The amount of numbers produced from decomposition or feature extraction may be too many to assign to the tactile interfaces, in which the dimensionality of the numbers may be reduced.

According to yet another embodiment, a computer program product may include a non-transitory computer readable medium having code to perform the steps of receiving samples of a data signal; transforming the samples from a time domain to a space domain; compressing the transformed samples; and/or generating control signals for operating an array of tactile interface devices by mapping the compressed samples to individual devices of the array of tactile interface devices.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the disclosed system and methods, reference is now made to the following descriptions taken in conjunction with the accompanying drawings.

DETAILED DESCRIPTION

Figure 1:
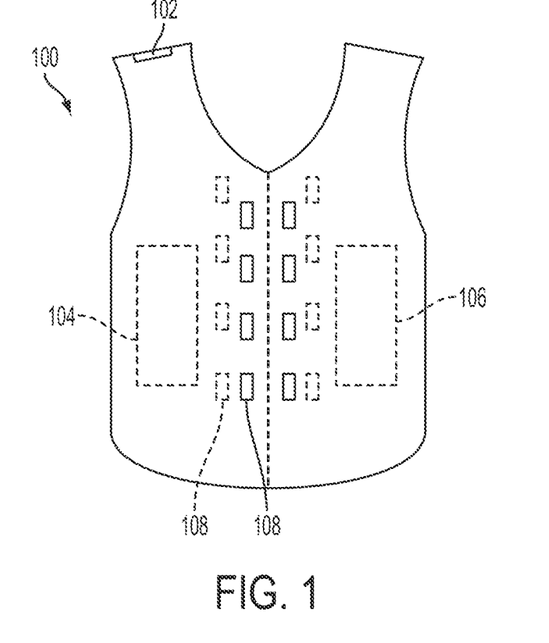
FIG. 1 is an illustration showing a vest with tactile interface devices configured to provide information transfer through somatosensation according to one embodiment of the disclosure.

FIG. 1 is an illustration showing a vest with tactile interface devices configured to provide information transfer through somatosensation according to one embodiment of the disclosure. A data-to-touch system may include a vest 100 having an array of tactile interface devices 108 located on a front and back of the best 100. Also mounted to the vest 100 may be a microcontroller 104, which receives data from an input device 102, such as a microphone, and converts the data into somatosensation feedback for output by the array of tactile interface devices 108. The vest 100 may also include battery pack 106 for operating the microcontroller 104 and the array of tactile interface devices 108. The input device 102 may include other devices, such as data sensors, including a GPS compass, a camera, and/or a network adapter configured to receive a data signal, such as through a cellular or other wireless connection, in addition or in the alternative to a microphone.

When the input device 102 is a microphone, the microcontroller 104 may process audio signals received by the microphone and generate signals for activating various devices of the array of tactile interface devices 108. The tactile interface devices 108 may be activated in a predictable manner based on the detected audio signal. Thus, a user wearing the vest 100 may learn to associate patterns generated in the array of tactile interface devices 108 with particular audible sounds. For example, a user may recognize a particular feedback from the devices 108 with a fire alarm or emergency vehicle sound, and even to fully understand another person's speech. The array of tactile interface devices 108 may include tactile and/or haptic interfaces, which may line the inside of an article of clothing, such as the vest 100. The tactile interface devices may include Eccentric Rotating Mass (ERMs) motors, Linear Resonant Actuators (LRAs), Piezoelectric Actuators, Voice/Speaker Coil Actuators, and/or Electrotactile Stimulators (wire leads).

Figure 2:
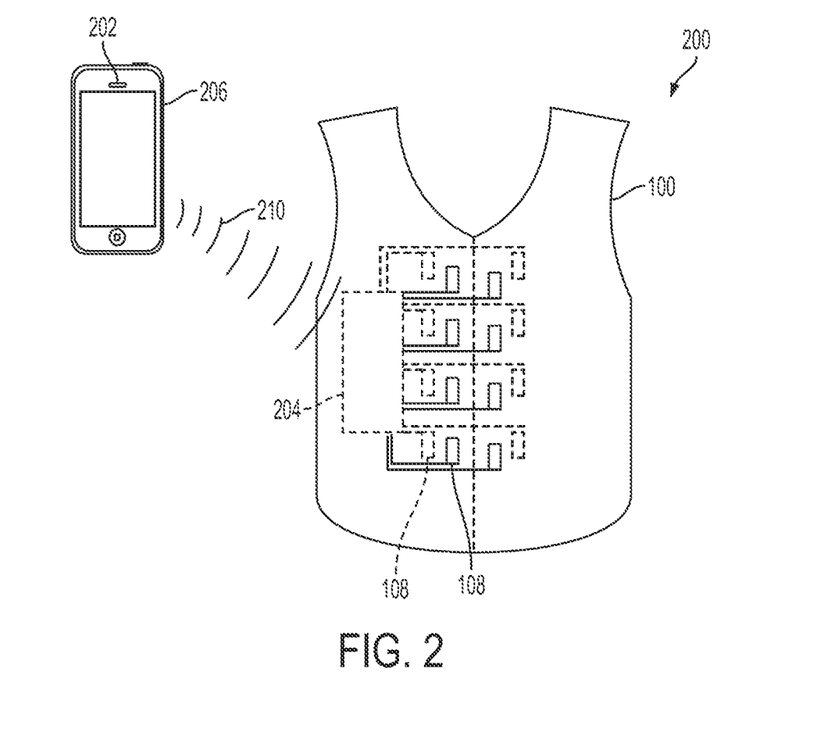
FIG. 2 is an illustration showing a vest with tactile interface devices configured to provide information, received from a smart phone, to a user through somatosensation according to one embodiment of the disclosure.

In another embodiment, the processing of audio signals may be performed by a computing device separate from the vest 100. For example, a user's computing device, such as a smart phone, may communicate with the vest 100 to provide control signals for activating the array of tactile interface devices 108. FIG. 2 is an illustration showing a vest with tactile interface devices configured to provide information, received from a smart phone, to a user through somatosensation according to one embodiment of the disclosure. The vest 100 may include a combined battery pack and microcontroller 204 coupled to the array of tactile interface devices 108. The microcontroller 204 of system 200 may be less sophisticated than the microcontroller 104 of FIG. 1, because some signal processing may be offloaded to a user's computing device 206. The computing device 206, such as a smart phone, may include a microphone 202 for detecting ambient sounds. The computing device 206 may process received audio signals to generate control signals that are transmitted to the microcontroller 204 through a connection 210. The connection 210 may be a low-power wireless connection, such as a Bluetooth connection, or any other suitable communications connection that is either wired or wireless.

The computing device 206 may be responsible for gathering data either via a connection to the Internet, or through integrated sensors, including a camera, a microphone, and/or an accelerometer. The device 206 may also perform computational processing on the data. After the information is processed, the phone may write data-frames, including control signals that instruct the microcontroller 204 how to present the information to the user through the array of tactile interface devices 108.

The microcontroller 204 may be part of a control board (not shown) that may be responsible for regulating/providing power to the array of tactile interface devices 108. The control board may also include a Bluetooth interface, or other communications interface, for collecting and processing data-frames from the computing device 206. The microcontroller 204 may receive the data-frames and modulate the array of tactile interface devices 108 based, at least in part, on control signals contained in the received data-frames. In one embodiment, the array of tactile interface devices 108 may be controlled through Pulse Width Modulation (PWM). In another embodiment, the array of tactile interface devices 108 may be controlled through custom-generated signals through digital-to-analog converters (DAC or D2A). The control board may also include a wireless transmitter for forwarding data-frames to other control boards, such as through I2C protocol, Bluetooth, or ZigBee.

Figure 3:
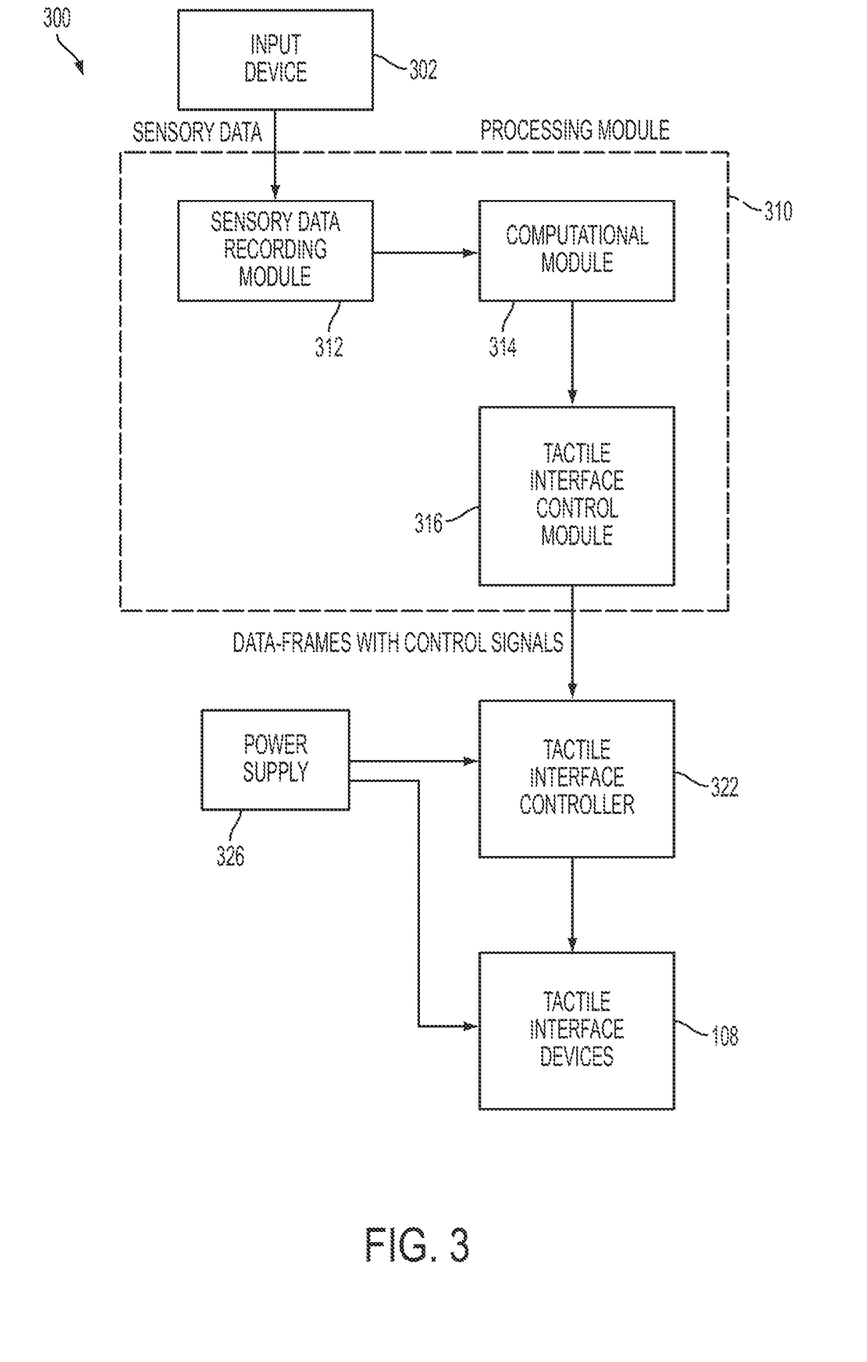
FIG. 3 is a block diagram illustrating a system configured to provide information transfer through somatosensation according to one embodiment of the disclosure.

Operation of a data-to-touch sensory substitution system, such as those described above, may be illustrated in a block diagram. FIG. 3 is a block diagram illustrating a system configured to provide information transfer through somatosensation according to one embodiment of the disclosure. An input device 302 may receive data for conveyance to a user of the data-to-touch system. The input device 302 may be, for example, a microphone configured to receive ambient sounds around the user. The input device 302 may also be, for example, a network interface configured to receive data from a remote source, such as the Internet.

A processing module 310 may be coupled to the input device 302 and to a tactile interface controller 322. The processing module 310 processes the data from input device 302 and generates control signals to instruct the tactile interface controller 322 to activate the tactile interface devices 108. A power supply 326 may be coupled to the tactile interface controller 322 and/or the tactile interface devices 108. The power supply 326 may be located on the vest and power the controller 322 and the devices 108. The power supply 326 may also power the processing module 310 and the input device 302 when those components are located on the vest. When the processing module 310 and input device 302 are separate from the vest, such as when integrated with a smart phone, a separate power supply (not shown) may power the processing module 310 and the input device 302.

The processing module 310 may include several modules for performing different operations on data received from the input device 302. A sensory data recording module 312 may record sensory data from the environment and/or data from the Internet into a buffer (not shown). A computational module 314 may transform, compress, and/or encode data recorded by the sensory data recording module 312. The computation module 314 may output data to a tactile interface control module 316, which generates data-frames for playback to the skin by the controller 322. In one embodiment, the data-frames provide near real-time playback of sensory data by the tactile interface devices 108.

Data-frames generated by the processing module 310 may be transmitted to the tactile interface controller 322. In one embodiment, the processing module 310 may reside on the computing device 206 of FIG. 2. For example, the processing module 310 may include microprocessors programmed to perform specific tasks or the processing module 310 may include computer program code that when executed by a general purpose computer processing unit (CPU) may configure the CPU to perform specific tasks. The tactile interface controller 322 may receive the encoded data-frames from the processing module 310 and control the tactile interface devices 108, by turning them on and off, modulating their intensity (such as frequency or amplitude of vibration, or magnitude of electrical stimulation), encoding more complex patterns to induce a sensation of texture, and/or combining actions of multiple tactile interface devices through coordination to produce sensations of sweeps, according to control signals in the received data-frames.

In one example operation of a system 300 of FIG. 3, a sound from the environment may be recorded via a microphone of a smartphone, such as the input device 302. The smartphone may include processing module 310 that transforms, compresses, and/or encodes frames of audio (in near real-time) as data-frames for tactile playback to the skin. The smartphone then transmits these data-frames to the tactile interface controller over a Bluetooth link. The controller 322 may then turn on and off and modulate the tactile interface devices 108 based on the data-frames. The tactile interface devices 108 may stimulate touch receptors in the skin, which send information to the brain via electrical impulses from the peripheral nervous system to the brain. The tactile interface devices 108 may be remapped in the processing module 310 to provide arbitrary layouts, such as tonotopic layouts and/or anti-tonotopic layouts of the tactile interface devices 108 in clothing, whether a vest or other clothing such as gloves, shirts, jackets, etc.

Figure 4:
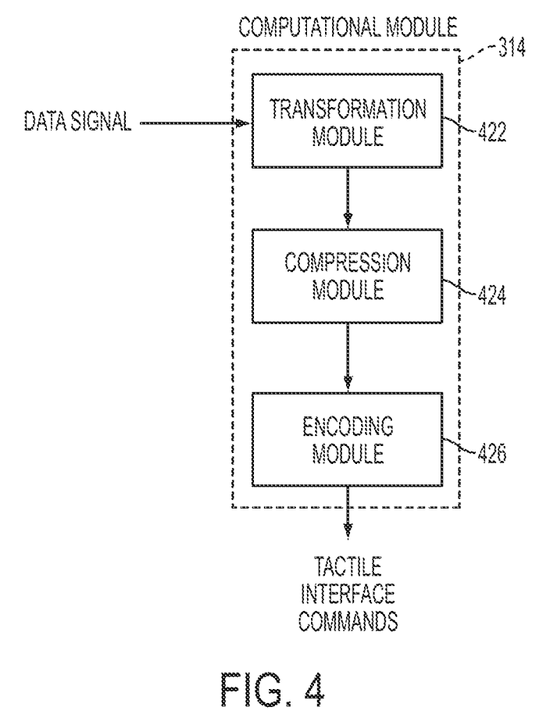
FIG. 4 is a block diagram illustrating a computational module for signal processing of data to provide information transfer through somatosensation according to one embodiment of the disclosure.

Further details regarding the computational module 314 are shown in FIG. 4. FIG. 4 is a block diagram illustrating a computational module for signal processing of data to provide information transfer through somatosensation according to one embodiment of the disclosure. The computational module 314 may include modules for processing and interpreting sensory data recorded in the recording module 312. For example, the computation module 314 may include a transformation module 422, a compression module 424, and/or an encoding module 426.

Sending information that has a faster sampling rate or frame-rate than what the skin can support (such as speech audio or stock trading data being streamed from the Internet) provides challenges not encountered by other sensory substitution devices, such as vision-to-touch systems. For example, raw speech (auditory) information may be too fast (0.125 ms/sample) for the skin's temporal acuity (~5-10 ms). In contrast, visual information can be provided at durations as slow as 40 ms, which is within the detection capabilities of skin. In one embodiment, the data for somatosensation may be transformed to trade off time for space—in other words, the spatial pattern of a high number of tactile interfaces (e.g. motors) can be used to summarize an underlying time-window of fast-changing information.

The transformation may be performed by transformation module 422. For example, a number of audio samples may be buffered and then transformed or parameterized to a set of values in such a way that these values represent the information contained for all of the samples. The resulting values may be fixed over the duration of the collected samples. In one embodiment, 128 samples of 8 kHz sampled speech audio may be buffered, and then parameterized values extracted from the signals. The values may be fixed over this 16 ms period. Thus, the skin's temporal acuity constraint may be overcome when the data is transformed. In different embodiments, transformation may involve a mathematical transformation, such as but not limited to a Discrete Cosine Transform (DCT), or a parameterized modeling of the signal, such as but not limited to Linear Predictive Coding (LPC). Transforms are a lossless mathematical conversion that may trade off time for space and may retain all of the information from the original signal. Parameterized models are lossy but may still produce close approximations of the information contained in the buffered data signal.

Because skin has a much lower temporal acuity (slower response) than that of the ear, the transformation module 314 may transform the incoming single-dimensional fast-varying sound signal to a multi-dimensional space that varies slow enough for the skin to perceive. Conventional "tactile hearing aids," such as those referred to in the background, process audio signals by splitting the audio signal into multiple channels using band-pass filtering. The conventional band-pass processing does not change the dimensionality or compress the audio signal as performed in certain embodiments of the present audio-to-speech system.

One method of transforming data performed by the transformation module 422 may be feature extraction, such as by use of Linear Predictive Filtering/Coding (LPC). An incoming digitally-sampled signal may be buffered into frames of samples, where the duration of the frame is longer than the acuity of the skin and tactile interfaces. A certain number of samples may correspond to a frame, and after that number of samples is buffered, processing and transformation may be performed on the frame. For each framed signal, a set of filter coefficients and a simple source signal may be derived. When the source signal is passed through the filter (defined by the derived coefficients), an estimate of the original signal may be reconstructed. The filter coefficients may remain fixed for the duration of each frame. The parameters for the LPC transformation may include a set of predictive filter coefficients, the energy of the frame, whether or not the frame was voiced, and an estimated fundamental pitch. In one embodiment, only the coefficients and energy may be stored from the LPC transformation. In other embodiments, feature extraction may be performed with other techniques, such as with a neural network. In such a neural network, the output layer may be used to represent different phonemes. The neural network may then be trained such that the output of the network gives a probability for each phoneme in the input data. The neural network output may then be passed through dimensionality reduction and mapped to tactile feedback devices.

Another method of transforming data performed by the transformation model 422 may include signal decomposition. Signal decomposition may begin with digitally-sampling an audio signal into frames with further processing performed on each frame. The signal may then be decomposed into a combination of a fixed set of basis functions. The set of basis functions may remain invariant from frame to frame, while the amount of each basis function present in the original signal may vary from frame to frame. An example of a signal decomposition is the Fast Fourier Transform (FFT), which decomposes a signal into a sum of sine functions of different frequencies. Other examples of signal decomposition may include Discrete Cosine Transform (DCT), which is similar to FFT but uses a cosine basis function, Wavelet Transform, which is similar to DCT but allows use of a number of different or custom basis functions that are parameterized by how stretched they are in time as opposed to frequency, and Autoencoding Neural Networks, which learn an optimal set of basis functions to represent some training data, parameterized by a desired output dimensionality. In such a neural network, the input layer (the original signal) is fed through a network containing a hidden ("encoding") layer (the representation to later be used for tactile feedback) and an output ("decoding") layer that attempts to match the input given the training data. After training, new incoming data fed through the neural network hidden layer may then be passed through dimensionality reduction and mapped to tactile feedback devices.

After the signal has been transformed or modeled by transformation module 422, the transformed data may be passed to a compression module 424 to reduce the output dimensionality of the signal. That is, after the information conveyed by the original audio signal has been sufficiently reduced in time by the transformation algorithm, the resulting dimensionality may be larger than can be represented by the array of tactile interface devices that are available in the system. A dimensionality reduction by compressing the transformed signals may reduce the dimensionality to a size appropriate for the tactile interface devices. Additionally, in some embodiments, the range of values for each dimension may exceed a number of different values the skin can discriminate. For example, a given dimension may vary between 0 and 1 with all real numbers in-between. However, when the tactile interface device is an eccentric rotating mass motor (ERM), the skin may only be able to discriminate between 8-16 different intensity levels. Quantizing the range of possible values for each dimension to 8-16 possible discrete values from 0 to 1 may further compress the transformed audio signal for the tactile interface devices.

In one example of quantization, the compression module 424 may limit the range of possible values that can be represented to suit the skin. When the data is speech, the natural statistics of speech may be used to determine a desired grouping dimensions of output dimensions and compress the data. As an example, to determine one possible allocation of frequency bands for a Discrete Cosine Transform (DCT)-based transform: for each collapsed bin, 2 hours of sampled natural speech audio may be broken into 16 ms frames (128-point, 8 kHz sampled) on which a DCT is taken. For each output, the five bins with the most energy are appended to a vector. These peak frequencies may be presumed to represent the most important formants, such as spectral energy sweeps that make up phonemes, the fundamental building blocks of speech. A 27-cluster 1-D K-means clustering algorithm may then be applied to the peak frequency observations to yield a frequency binning listing the bins that capture the most relevant speech information. In this example, the number of tactile interface devices may be reduced from 128 components to 27 components through the compression algorithm.

Other examples of quantization may include linear mapping, trained statistical mapping by dimension, and global trained statistical mapping. In linear mapping, level assignments may be divided. For example, if a dimension can take on values [0 1], the [0 1] values may be quantized to N steps (e.g. 0, 0.25, 0.75, 1). These steps may be evenly spaced. In trained statistical mapping by dimension, quantization includes examining a resulting histogram of some training data for each dimension and then determining an uneven spacing of levels based on equal units of area underneath the histogram. In global trained statistical mapping, steps similar to trained statistical mapping by dimension are performed, but the histogram of observations is taken across all dimensions, such that all dimensions use the same level spacings.

In one example of reducing dimensionality, K-Means clustering for transformed data may be performed by the compression module 424. K-Means processing may be applied to a frequency-parameterized transform performed by the transformation module 422, such as an FFT, to find the most relevant frequency locations based, at least in part, on some training examples. After having determined a set of the K most relevant frequency locations, the frequency bins generated by the transformation module 422 may be reduced to K larger bands by the compression module 424.

In another example of reducing dimensionality, auto-encoding neural networks may wrap dimensionality reduction into the transformation phase itself. In this example, an optimal set of basis functions parameterized by a desired dimensionality may be derived by training an autoencoder neural network.

After an audio signal is processed by transformation module 422 and/or compression module 424, the resulting data may be applied to the skin through the actuation of tactile interface devices. An encoding module 426 may receive the data and generate control signals for the tactile interface devices, which map the data signals to tactile interface devices. The mapping may be based, at least in part, on a physical layout for the tactile interface devices, which may be customized to enhance acuity for certain applications.

In one example of mapping the data to tactile interface devices, decomposition-based transform processing may be performed by the encoding module 426. In this example, a 1:1 mapping is obtained where each tactile interface device is assigned to one dimension of output. The tactile interface device may be actuated monotonically based on the quantized value of the data. For example, if a dimension of output has a value of zero, the element is turned off. If the dimension is the maximum quantized value, the element may be actuated at a maximum level. The encoding module 426 may generate data-frames with control signals to activate tactile interface devices according to the mapping. For example, the encoding module 426 may generate a data-frame containing a device identifier that identifies a particular tactile interface device on the vest and containing an intensity value and a time value to indicate how long and how strongly to provide feedback through the identified device.

In another example of mapping the data to tactile interface devices, each dimension of output may be assigned to multiple tactile interfaces (a tactile interface "subset") that are placed in close proximity to one another. Within the subset, interfaces may be turned on and off in quick succession (at durations that subdivide the duration of the overall data frame) to give the sensation of a sweep across the skin. The directionality of the sweep may then be mapped to whether a value represented by the dimension of output is negative, positive, complex or real. The intensity of each element in the tactile interface subset may still be monotonically actuated with the magnitude of output of the data-frame.

In another example of mapping the data to tactile interface devices, Linear Predictive Filtering/Coding (LPC) may be performed by the encoding module 426. Each frame may produce a set of filter coefficients and an energy parameter. These coefficients may be converted to frequency-locations in a line spectral pair (LSP) representation, which may also be referred to as line spectral frequencies (LSFs). Unlike a decomposition transform where each dimension represents how much of a basis function is present, the LSPs specify where the most relevant frequencies are for each frame of audio. Any tactile elements that are turned on for a given frame may be assigned a stimulus intensity level that is mapped to the frame's quantized energy parameter. In one embodiment using LSP, all active devices are assigned the same intensity level within each frame. The intensity and active elements may vary from frame to frame, but within a single frame all active devices operate at the same intensity.

In a further example of mapping the data to tactile interface devices, single global axis mapping may be performed by the encoding module 426. In this example, the possible range of frequencies may be discretized to a set of bands based on the number of tactile interface devices in the array. Thus, each element may represent a band of frequencies. For each output frame, the nearest (in frequency-space) tactile element may be turned on for each LSP by control signals generated by the encoding module 426. For example, if there are six LSPs, six tactile elements may be turned on for each frame, unless LSPs happen to fall in the same quantized frequency band.

In another example of mapping the data to tactile interface devices, multiple local axis mapping may be performed by the encoding module 426. This mapping is similar to single global axis mapping, but each LSP is given a different set of tactile interface devices to represent a range of frequencies. For example, if there are six LSPs then there may be six axis.

In a further example of mapping the data to tactile interface devices, coded local axis mapping may be performed by the encoding module 426. This mapping is similar to multiple local axis mapping, in that each LSP is given a different set of axis representative of the frequency domain. However, tactile interface devices may be mapped to a frequency using a tree-type code. For example, a binary code with two levels (four tactile elements total) may be used for the tree-type code. The first two elements may represent a top-half and bottom of the entire frequency range. The next two elements may represent either the top two quarters or bottom two quarters as a function of the first level.

According to one embodiment, a pre-processing module (not shown) may perform signal processing operations on the data signal prior to the transformation module 422. Pre-processing may enhance the resulting output quality of subsequent processing by the transformation module 422, the compression module 424, and the encoding module 426. Pre-processing may include, for example, noise reduction. Pre-processing may also include, for example, gating such that if the overall energy of the data signal is below a threshold within a given analysis window or data frame, the data signal may be zeroed for that window. Pre-processing may further include spectral subtraction, such that if the overall energy of the signal is below a threshold within a given analysis window or data frame, the spectral footprint of the signal's spectrogram is subtracted from subsequent frames.

A physical layout for the tactile interface devices may be stored in a file accessible by the encoding module 426 and used as part of the mapping process described above. For example, the smart phone 206 of FIG. 2 may receive an identification from the microcontroller 204 of a layout of the tactile interface devices 108 when the smart phone 206 first pairs with the microcontroller 204. Alternatively, the user may input to the smart phone 206 a layout of the tactile interface devices 108, such as by entering a model number of the vest. The physical layout of the tactile interface devices 108 may be selected to improve the relevance of information being mapped to the tactile interface devices.

The computational module 314 may be used to assist in the selection of a physical layout for the tactile interface devices. In one example of mapping the tactile interface devices for decomposition-based transforms, a 2-D tonotopic layout may be created that is agnostic of the type of decomposition used. First, training data may be passed through the transformation module 422 and the compression module 424 to obtain example signals. Then, a correlation matrix may be calculated for the data. Next, a dissimilarity/distance matrix may be calculated by subtracting from 1 the correlation matrix. Then, multi-dimensional scaling may be performed on this distance matrix to obtain a two-dimensional layout that is tuned to the natural statistics for speech audio. In another example of mapping the tactile interface devices for Linear Predictive Filtering/Coding (LPC), a column layout may be created for each axis. Then, as LSPs are produced in a sorted order, columns may be ordered from left-to-right by increasing frequency.

Figure 5:
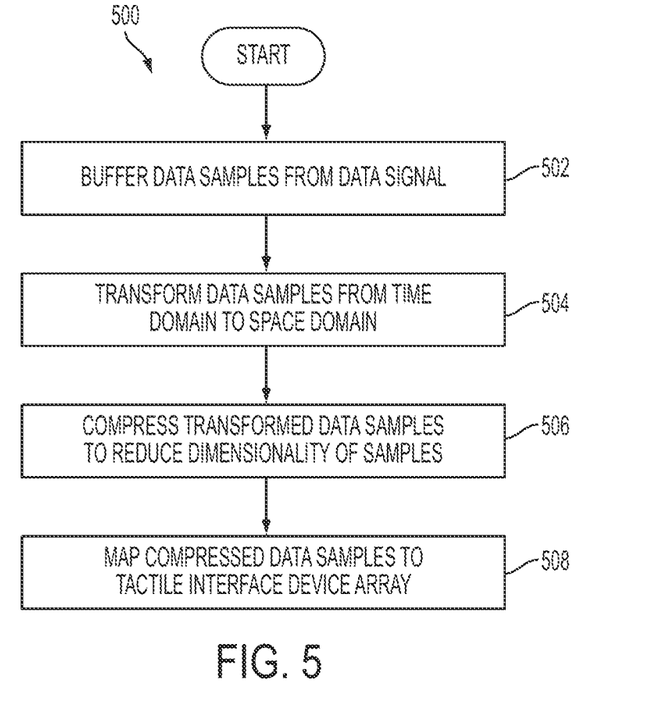
FIG. 5 is a flow chart illustrating a method for providing information transfer through somatosensation according to one embodiment of the disclosure.

One method performed by the computational module 314 is illustrated in FIG. 5. FIG. 5 is a flow chart illustrating a method for providing information transfer through somatosensation according to one embodiment of the disclosure. A method 500 begins with buffering data samples, such as audio samples, from a data signal at block 502. At block 504, the data samples of block 502 may be transformed from the time domain to the space domain. At block 506, the transformed data samples of block 504 may be compressed and/or quantized to reduce a dimensionality of the transformed data samples. Then, at block 508, the compressed data samples may be mapped to tactile interface devices. Control signals for the tactile interface devices may be generated from the mappings of block 508.

The method 500 of FIG. 5 may operate on the computational module 314 to process, for example, audio signals or any other type of data. Processing of non-audio data may be similar to that described above with reference to FIG. 5 and the other figures presented herein. In general, data processing by the processing computation module 314 may include representation processing, transformation processing if the data is too fast for skin, dimensionality reduction processing if dimensionality exceeds the number of tactile interface devices, and/or quantization based on representation capability of each tactile interface device.

Non-audio data in an information stream, agnostic of source, may be adapted to be represented as a numerical N-dimensional time-varying stream of data, where each sample-point contains N-values. For example, if a user is observing ten stocks, a 10-dimensional time-varying stream may be produced. Stocks and other data, such as temperature weather data, begin as numerical data. Non-numerical data, such as whether the weather condition is cloudy, raining, or sunny, may be considered categorical variables that can be represented in numerical variables based on a mapping. For example, clouds=−1, raining=0, and sunny=1.

After the non-audio data is represented as numerical data, the data may be transformed. For example, agnostic to the source of data, a DCT may collect up N-samples and translate them to an N-dimensional sample, where the information may be fixed for the duration of those N-Samples. In the stock market example, where a user is tracking 10 stocks, an N-point 1-D DCT may be applied to each stock, which produces a 10×N dimensional output. Alternatively, a 10-D DCT may be applied to the stock data. Although DCT is used as an example, other methods, such as autoencoding neural networks, may be used to transform non-audio data.

After transforming the non-audio data, the dimensionality may be reduced through compression if the signal is highly dimensional and there are a limited number of tactile interface devices. Speech data may be transformed into a high-dimensional signal because a large number of samples are collected in an effort to "slow down" the information rate for skin. A similar issue arises for certain non-audio data, such as stock market or weather data where a large number of stocks or weather locations are being tracked. Dimensionality reduction may be accomplished through a number of methods, such as Dictionary Coding with K-Means as described above, using K-Means to find the most important dimensions to collapse to such as used in the DCT, through a parameter of autoencoding neural networks, or through Singular Value Decomposition (SVD).

After representing data, transforming the data, and/or compressing the data, the resulting data may be quantized for the tactile interface devices. Quantization may be performed by statistical processes, such as histogram sweeping and K-Means averaging. In histogram sweeping, data may be processed and for each dimension, a histogram of the resulting samples may be generated. Quantization boundaries may be derived as equal area regions, where the area is defined by the number of values to represent. In K-Means averaging, data may be processed and, for each dimension, a histogram of the resulting samples may be generated. Then, the number of clusters may be set to be the number of output values capable of being represented by the tactile interface device. K-Means may be performed on the histogram for each dimension by running multiple times, each time with different cluster centroid initializations, and averaging the sorted results. The 1-D centroids may be quantized values to use for mapping the unquantized data. After quantizing the data, the data may be mapped to the tactile interface array.

Figure 6:
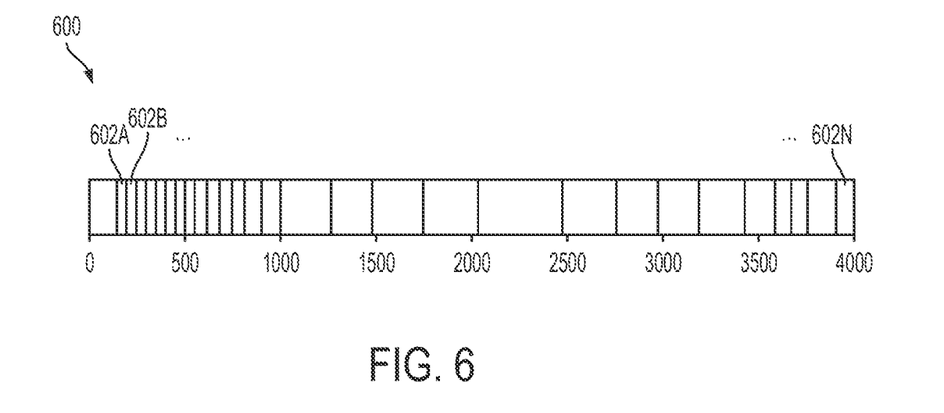
FIG. 6 is a graph illustrating assignment of frequency bins according to one embodiment of the disclosure.

Referring back to FIG. 5, block 508 describes the mapping of data to tactile interface devices. An illustration of the mappings of various frequencies of audible speech to tactile interface devices is shown in FIG. 6. FIG. 6 is a graph illustrating assignment of frequency bins according to one embodiment of the disclosure. A spectrum 600 shows a range of frequencies between 0 to 4000 Hertz common to speech audio. The spectrum 600 may be divided into bins 602A, 602B, . . . , 602N. Each of the bins may be assigned to a tactile interface device. For example, if there are 10 tactile interface devices there may be 10 frequency bins. A quantized value for each of the bins 602A-N may be generated by the compression module 424 of FIG. 4. The quantized value for those bins may be used by the encoding module 426 to generate control signals to activate, at various levels corresponding to the quantized value, the corresponding tactile interface devices by mapping those signals to tactile interface devices.

The bins 602A-N of FIG. 6 may be selected based on natural statistics of speech. In one example, if DCT transformations are used, data may be produced sorted by frequency. The grouping or layout of bins 602A-N may then be ordered accordingly. More generically, recorded speech across different speakers may be processed through the compression module 424 to produce N-dimensional frames of data and identify statistically how dimensions co-occur with one another. A selection of frequency bins 602A-N and a corresponding physical layout of tactile interface devices may be generated such that dimensions that tend to co-occur are placed close together, and those that tend to not co-occur are spaced further apart, or vice-versa.

Figure 7:
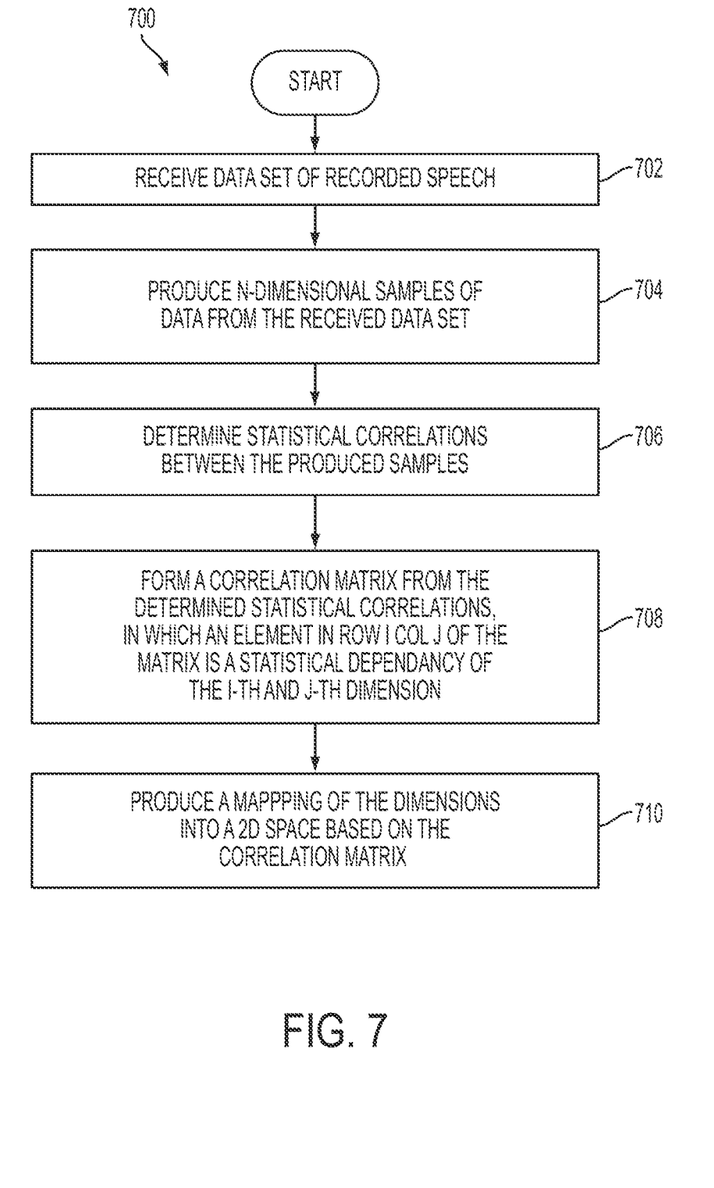
FIG. 7 is a flow chart illustrating a method for developing a mapping of frequency bins to individual tactile interface devices of an array of tactile interface devices according to one embodiment of the disclosure.

The selection of locations for bins 602A-N may be performed in non-real time and stored as a configuration file for reference. FIG. 7 is a flow chart illustrating a method for developing a mapping of frequency bins to individual tactile interface devices of an array of tactile interface devices according to one embodiment of the disclosure. A method 700 begins at block 702 with receiving a data set of recorded speech. At block 704, N-dimensional samples of the data of block 702 may be produced by the computational module 314. At block 706, statistical correlations are determined between the samples. At block 708, the processed data frames may be used to calculate a correlation matrix. The correlation matrix may be an N×N matrix, where an element in row i col j is a measure of the statistical dependency of the ith and jth dimensions. The correlation matrix is subtracted from 1, if co-occurring dimensions are to be physically placed closer to one another. The resulting correlation matrix provides a notion of distance or dissimilarity. At block 710, the correlation matrix may be processed by a Multi-Dimensional-Scaling (MDS) algorithm to find a physical layout for where each dimension should be placed in a 2-D space corresponding to locations of the tactile interface devices.

Figure 8:
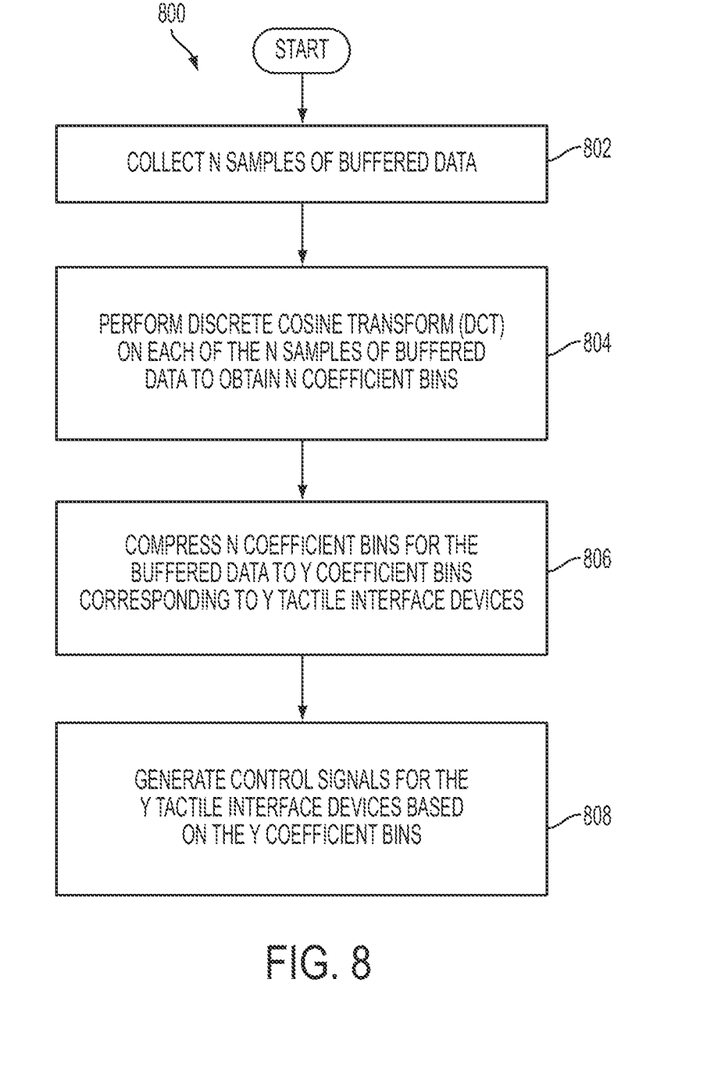
FIG. 8 is a flow chart illustrating a method of processing data for providing information transfer through somatosensation using a transform according to one embodiment of the disclosure.

Referring back to FIG. 5, the method 500 describes a generic process for mapping audio-to-touch sensory substitution. One specific method for performing high-throughput sensory substitution using Discrete Cosine Transform (DCT) is described with respect to FIG. 8. FIG. 8 is a flow chart illustrating a method of processing data for providing information transfer through somatosensation using a transform according to one embodiment of the disclosure. A method 800 begins at block 802 with collecting N samples of buffered data, such as collecting 128 sample frames of 8 kHz sampled audio. At block 804, a DCT is performed on each of the N samples of buffered data to obtain N coefficient bins. When, the DCT is performed on 128-sample frames, the DCT produces 128 temporally static coefficients "bins." In one embodiment, negative coefficients may be set to zero (for tactile mapping purposes). At block 806, the N coefficient bins for the buffered data may be compressed to Y coefficient bins corresponding to Y tactile interface devices. In one embodiment, the coefficients may each be quantized to N bits ($2^N$ possible values), which are then mapped to a tactile stimulus intensity for each tactile interface device. At block 808, control signals may be generated for the Y tactile interface devices based on the Y coefficient bins of block 806.

The compression of block 806 may include dimensionality reduction based on a clustering algorithm, such as a K-Means algorithm. In the case of the DCT, the dimensionality reduction may include accessing a configuration file generated offline (in non-real time). The configuration file may be created by accessing a large data set of recorded speech and performing an N-Sample DCT across the data, which produces N-dimensional frames of data. For each frame, Z dimensions/indices may be found containing the largest values and those indices appended into a list/vector. This list may be a 1-D list, where each index is not representative of a dimension but of a sample. A K-Means clustering algorithm may then be executed on this list to form Y clusters, thus finding a set of Y representative DCT indices to represent the data.

In one example, there are 128 bins (ordered from index 0 to index 127) and the K-Means algorithm may select the indices Y=[5, 19, 94, 120]. Then, for each incoming 128-sample frame of data, a 128-pt DCT is processing to generate a data frame with 128 bins. A L1/L2 distance is used to collapse each bin into the nearest representative bin Y. Thus, the values in bins 0, 1, 2, 3, 4, 5, 6, 7, 8, 9, 10, 11 (the closest bins to 5 from Y) may be collapsed to a single value, which may be either an average value, a weighted average, a max value, a median value, or any other statistically generated value from that set. The process may be repeated for the other indices identified by the K-Means algorithm.

Figure 9:
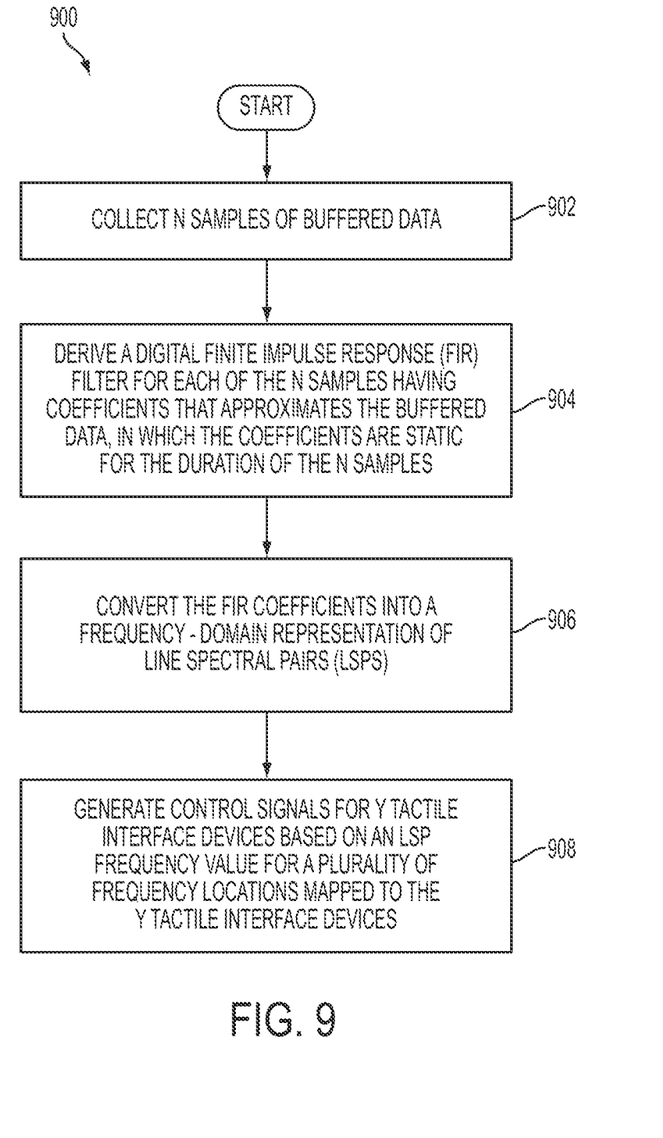
FIG. 9 is a flow chart illustrating a method of processing data for providing information transfer through somatosensation using linear predictive coding (LPC) according to one embodiment of the disclosure.

Although FIG. 8 represents one specific application of the method 500 of FIG. 5 using DCT, other processing may be used within the method 500 of FIG. 5. For example, performing high-throughput sensory substitution may be performed with linear predicting coding (LPC) as described with reference to FIG. 9. FIG. 9 is a flow chart illustrating a method of processing data for providing information transfer through somatosensation using linear predictive coding (LPC) according to one embodiment of the disclosure. A method 900 may include at block 902 collecting N samples of buffered data. At block 904, a digital finite impulse response (FIR) filter may be derived for each of the N samples, each filter having coefficients that approximate the buffered data. In one embodiment, the coefficients may be static for the duration of the N samples. These filter coefficients may be used to reconstruct a close approximation of the input original signal. At block 906, these filter coefficients may be converted to a frequency-domain representation of Line Spectral Pairs (LSPs), which represent frequency locations. A set of tactile interface devices may represent a quantized array of frequencies, in which for each LSP frequency value in a given frame, a representative tactile interface device may be turned on based on control signals generated at block 908.

Beyond applications for hearing, the data-to-touch system described above creates a generalized framework for designing devices to send streams of information to the brain for sensory processing via unusual sensory modalities. The system described above may convey information including weather data, stock market data, biological signatures (glucose levels, heart-rate, etc.) of one's self, another individual, or groups of individuals, social media data (e.g. message feeds), and/or sensory information outside the range of normal perception (e.g. supersonic or subsonic auditory information).

Figure 10:
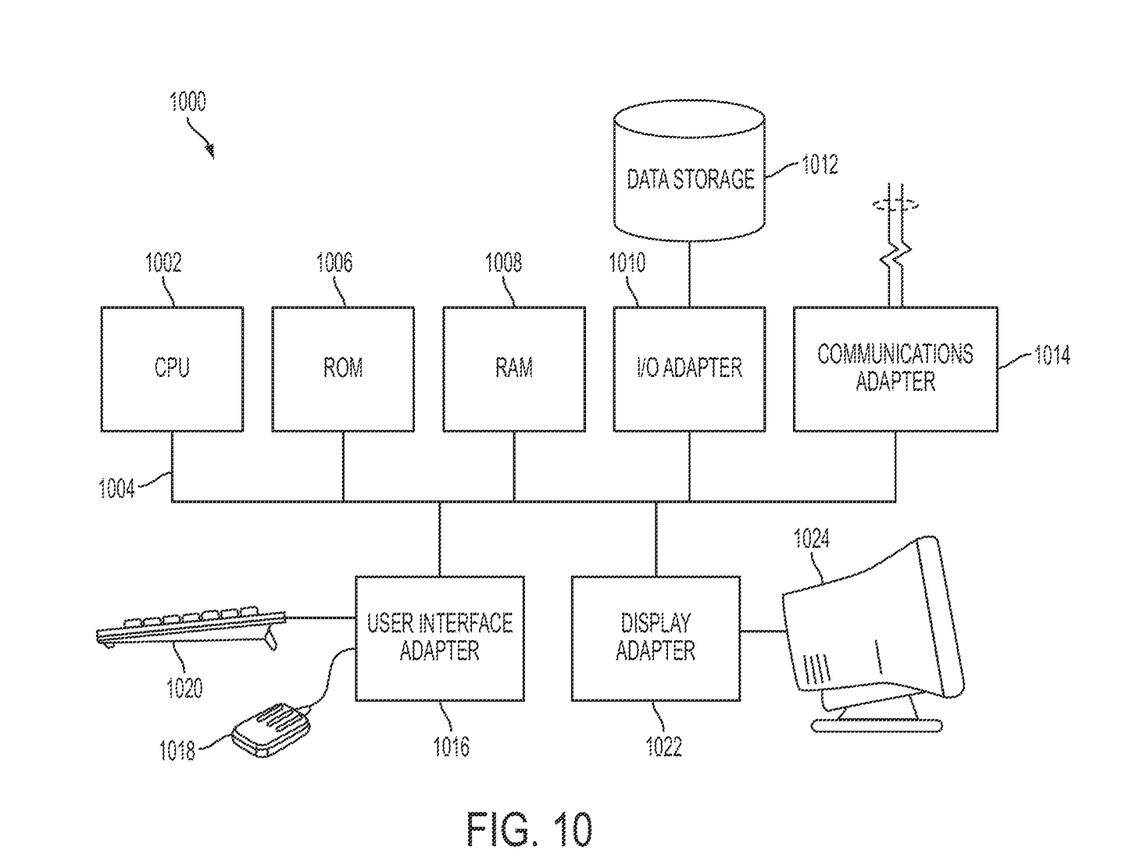
FIG. 10 is a block diagram illustrating a computer system according to one embodiment of the disclosure.

FIG. 10 illustrates a computer system 1000 adapted according to certain embodiments of the computing device 206 of FIG. 2 or microcontroller 104 of FIG. 1. The central processing unit ("CPU") 1002 is coupled to the system bus 1004. Although only a single CPU is shown, multiple CPUs may be present. The CPU 1002 may be a general purpose CPU or microprocessor, graphics processing unit ("GPU"), and/or microcontroller. The present embodiments are not restricted by the architecture of the CPU 1002 so long as the CPU 1002, whether directly or indirectly, supports the operations as described herein. The CPU 1002 may execute the various logical instructions according to the present embodiments.

The computer system 1000 may also include random access memory (RAM) 1008, which may be synchronous RAM (SRAM), dynamic RAM (DRAM), synchronous dynamic RAM (SDRAM), or the like. The computer system 1000 may utilize RAM 1008 to store the various data structures used by a software application. The computer system 1000 may also include read only memory (ROM) 1006 which may be PROM, EPROM, EEPROM, optical storage, or the like. The ROM may store configuration information for booting the computer system 1000. The RAM 1008 and the ROM 1006 hold user and system data, and both the RAM 1008 and the ROM 1006 may be randomly accessed.

The computer system 1000 may also include an input/output (I/O) adapter 1010, a communications adapter 1014, a user interface adapter 1016, and a display adapter 1022. The I/O adapter 1010 and/or the user interface adapter 1016 may, in certain embodiments, enable a user to interact with the computer system 1000. In a further embodiment, the display adapter 1022 may display a graphical user interface (GUI) associated with a software or web-based application on a display device 1024, such as a monitor or touch screen.

The I/O adapter 1010 may couple one or more storage devices 1012, such as one or more of a hard drive, a solid state storage device, a flash drive, and a compact disc (CD) drive to the computer system 1000. According to one embodiment, the data storage 1012 may be a separate server coupled to the computer system 1000 through a network connection to the communications adapter 1014. The communications adapter 1014 may be adapted to couple the computer system 1000 to the network, which may be one or more of a LAN, WAN, and/or the Internet. The user interface adapter 1016 may couple user input devices, such as a keyboard 1020, a pointing device 1018, and/or a touch screen (not shown) to the computer system 1000. The keyboard 1020 may be an on-screen keyboard displayed on a touch panel. The display adapter 1022 may be driven by the CPU 1002 to control the display on the display device 1024. Any of the devices 1002-1022 may be physical and/or logical.

The applications of the present disclosure are not limited to the architecture of computer system 1000. Rather the computer system 1000 is provided as an example of one type of computing device that may be adapted to perform the functions of the computing device 206 or microcontroller 104 of FIGS. 1 and 2. For example, any suitable processor-based device may be utilized including, without limitation, personal data assistants (PDAs), tablet computers, smartphones, computer game consoles, and multi-processor servers. Moreover, the systems and methods of the present disclosure may be implemented on application specific integrated circuits (ASIC), very large scale integrated (VLSI) circuits, or other circuitry. In fact, persons of ordinary skill in the art may utilize any number of suitable structures capable of executing logical operations according to the described embodiments. For example, the computer system may be virtualized for access by multiple users and/or applications.

If implemented in firmware and/or software, the functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and blu-ray discs. Generally, disks reproduce data magnetically, and discs reproduce data optically. Combinations of the above should also be included within the scope of computer-readable media. Additionally, the firmware and/or software may be executed by processors integrated with components described above.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An apparatus, comprising:
    an input device;
    a processing module configured to control an array of tactile interface devices and coupled to the input device, wherein the processing module is configured to control the array of tactile interface devices by performing the steps of:
        receiving samples of a data signal from the input device;
        selecting a window of samples from the received samples of the data signal;
        transforming the data samples of the window of samples into spatial patterns by transforming an N-dimensional signal of a first rate within the window of samples into a higher K-dimensional signal of a second slower rate, wherein the second rate corresponds to a rate capable of conveyance to a user through the array of tactile interface devices; and
        generating control signals for operating the array of tactile interface devices by mapping the spatial patterns to one or more devices of the array of tactile interface devices.

2. The apparatus of claim 1, wherein the processing module is configured to transform the data samples into special patterns by transforming the data samples from a time domain to a space domain, and wherein the processing module is further configured to compress the transformed data samples to reduce a dimensionality of the data samples.

3. The apparatus of claim 1, wherein the tactile interface devices comprise at least one of eccentric rotating mass (ERM) motors, piezoelectric interfaces, and/or vibrating solenoids.

4. The apparatus of claim 1, wherein the input device comprises at least one of a microphone, a network adapter, and a camera.

5. The apparatus of claim 1, wherein the processing module comprises a smart phone, wherein the input devices comprises a microphone integrated with the smart phone, and wherein the data signal comprises an audio signal.

6. The apparatus of claim 1, further comprising a tactile interface microcontroller coupled to the array of tactile interface devices, wherein the tactile interface microcontroller is configured to receive the generated control signals and activate individual tactile interface devices of the array of tactile interface devices.

7. The apparatus of claim 1, wherein the processing module is configured to perform signal decomposition on the data samples.

8. The apparatus of claim 7, wherein the processing module is configured to transform the data samples with a discrete cosine transform (DCT) to obtain a set of coefficients, and wherein the processing module is further configured to compress the transformed data samples by reducing the resulting set of coefficients to a smaller second set of coefficients, wherein each of the second set of coefficients corresponds to a device in the array of tactile interface devices or may map to a more complex tactile pattern that spans multiple devices in the array of tactile interface devices.

9. The apparatus of claim 8, wherein the second set of coefficients are mapped to the array of tactile interface devices based on mapping data retrieved from a configuration file.

10. The apparatus of claim 1, wherein the processing module is configured to perform feature extraction on the data samples.

11. The apparatus of claim 10, wherein the processing module is configured to transform the data samples by deriving a digital finite impulse response (FIR) filter for one or more data samples, wherein the produced FIR filter for a data sample comprises coefficients that approximate the data sample, and wherein the processing module is configured to translate the predictive FIR coefficients for a data sample into a frequency-domain representation set of line spectral pairs (LSPs).

12. The apparatus of claim 11, wherein the processing module is configured to generate control signals by quantizing each LSP from the set of LSPs based on a mapping from this set to the array of tactile interface devices.

13. A method, comprising:
    receiving samples of a data signal, wherein the samples correspond to a window of time;
    transforming the samples from a time domain to a space domain to reduce a data rate of the samples, wherein the transformed samples are represented to a set of coefficients;
    compressing the set of coefficients representing the transformed samples to reduce a dimensionality of the transformed samples; and
    generating control signals for operating an array of tactile interface devices by mapping the compressed samples to one or more devices of the array of tactile interface devices.

14. The method of claim 13, wherein the step of receiving samples of a data signal comprises receiving audio samples of an audio signal.

15. The method of claim 13, wherein the step of transforming the samples comprises performing signal decomposition on the data samples.

16. The method of claim 15, wherein the step of transforming the samples comprises transforming the samples with a discrete cosine transform (DCT) to obtain a set of coefficients, and wherein the step of compressing the transformed samples comprises compressing the transformed samples by reducing the dimensionality of the resulting set of coefficients to a smaller second set of coefficients, wherein each of the second set of coefficients corresponds to one or more devices of the array of tactile interface devices.

17. The method of claim 16, further comprising:
    retrieving a configuration file comprising mapping data; and
    mapping the second set of coefficients to the array of tactile interface devices based on the mapping data, wherein the generated control signals are based, at least in part, on the mapping of the first or second set of coefficients to the array of tactile interface devices.

18. The method of claim 13, wherein the step of transforming the samples comprises transforming the samples using a digital filter.

19. The method of claim 18, wherein the step of transforming the samples comprises transforming the samples by deriving a digital finite impulse response (FIR) filter for a set of one or more samples, wherein the produced FIR filter for a sample comprises coefficients that approximate the sample, and wherein the step of compressing the samples comprises converting the predicted FIR coefficients for a sample into a frequency-domain representation set of line spectral pairs (LSPs).

20. The method of claim 19, wherein the step of generating control signals comprises quantizing each LSP from the set of LSPs based on a mapping from this set to the array of tactile interface devices.

21. A computer program product, comprising:
a non-transitory computer readable medium comprising code to perform the steps comprising:
receiving samples of a data signal;
transforming the samples from a time domain to a space domain to reduce a data rate of the samples;
compressing the transformed samples to reduce a dimensionality of the transformed samples; and
generating control signals for operating an array of tactile interface devices by mapping the compressed samples to individual devices of the array of tactile interface devices.

22. The computer program product of claim 21, wherein the step of receiving samples of a data signal comprises receiving audio samples of an audio signal.

23. The computer program product of claim 21, wherein the step of transforming the samples comprises performing signal decomposition on the data samples.

24. The computer program product of claim 23, wherein the step of transforming the samples comprises transforming the samples with a discrete cosine transform (DCT) to obtain a resulting set of coefficients, and wherein the step of compressing the transformed samples comprises compressing the transformed samples by reducing the resulting set of coefficients to a smaller second set of coefficients, wherein each of the second set of coefficients corresponds to one or more devices of the array of tactile interface devices.

25. The computer program product of claim 24, wherein the medium further comprises code to perform the steps of:
retrieving a configuration file comprising mapping data; and
mapping the second set of coefficients to the array of tactile interface devices based on the mapping data, wherein the generated control signals are based, at least in part, on the mapping of the first or second set of coefficients to the array of tactile interface devices.

26. The computer program product of claim 21, wherein the step of transforming the samples using a digital filter.

27. The computer program product of claim 26, wherein the step of transforming the samples comprises deriving a digital finite impulse response (FIR) filter for a set of one or more samples, wherein the produced FIR filter for a sample comprises coefficients that approximate the sample, and wherein the step of compressing the samples comprises converting the predicted FIR coefficients for a sample into a frequency-domain representation set of line spectral pairs (LSPs).

28. The computer program product of claim 26, wherein the step of generating control signals comprises quantizing each LSP from the set of LSPs based on a mapping from this set to the array of tactile interface devices.

* * * * *